United States Patent

Christian

[11] Patent Number: 5,931,162
[45] Date of Patent: Aug. 3, 1999

[54] VENTILATOR WHICH ALLOWS SPONTANEOUS INHALATION AND EXPIRATION WITHIN A CONTROLLED BREATHING MODE

[75] Inventor: Klaus Christian, Neckarbischofsheim, Germany

[73] Assignee: Siemens Aktiengesellschaft, Munich, Germany

[21] Appl. No.: 08/867,942

[22] Filed: Jun. 3, 1997

[30] Foreign Application Priority Data

Jun. 3, 1996 [SE] Sweden .................................. 9602199

[51] Int. Cl.$^6$ ............................ A61M 16/00; A62B 7/00; F16K 31/02
[52] U.S. Cl. ............................... 128/204.23; 128/204.18; 128/204.21; 128/204.26
[58] Field of Search ........................ 128/204.18, 204.21, 128/204.25, 204.26

[56] References Cited

U.S. PATENT DOCUMENTS

| | | |
|---|---|---|
| 3,976,064 | 8/1976 | Wood et al. . |
| 4,141,356 | 2/1979 | Smargiassi ........................ 128/204.23 |
| 4,206,754 | 6/1980 | Cox et al. .......................... 128/204.21 |
| 4,211,221 | 7/1980 | Schwanbom et al. . |
| 4,340,045 | 7/1982 | Manley .............................. 128/204.24 |
| 4,635,631 | 1/1987 | Izumi ................................ 128/204.23 |
| 4,928,684 | 5/1990 | Breitenfelder et al. ............ 128/204.21 |
| 4,945,899 | 8/1990 | Sugiyama et al. ................. 128/204.23 |
| 5,016,626 | 5/1991 | Jones ................................ 128/204.26 |
| 5,048,515 | 9/1991 | Sanso ................................ 128/204.26 |
| 5,099,837 | 3/1992 | Russel, Sr. et al. ............... 128/204.26 |
| 5,107,830 | 4/1992 | Younes .............................. 128/204.18 |
| 5,107,831 | 4/1992 | Halpern et al. .................... 128/204.26 |
| 5,129,390 | 7/1992 | Chopin et al. ..................... 128/204.21 |
| 5,303,700 | 4/1994 | Weismann et al. ................ 128/204.23 |
| 5,664,562 | 9/1997 | Bourdon ............................ 128/204.23 |
| 5,720,278 | 2/1998 | Lachmann et al. ................ 128/204.23 |
| 5,797,393 | 8/1998 | Kohl .................................. 128/204.23 |

OTHER PUBLICATIONS

Operating Manual for Servo Ventilator 300, Siemens–Elema AB, May 1993.

*Primary Examiner*—John G. Weiss
*Assistant Examiner*—Joseph F. Weiss, Jr.
*Attorney, Agent, or Firm*—Hill & Simpson

[57] ABSTRACT

A ventilator has an inspiration section for supplying respiratory gas to a respiratory system of a patient and an expiration section for conveying respiratory gas from the respiratory system is described. If the patient spontaneously inhales during a controlled inspiration phase, the inspiration section and expiration section will be controlled to allow a spontaneous exhalation during a specific period of time within the inspiration phase. The patient thus will be able to respirate in a natural way even during controlled respiration, resulting in increased comfort and increased motivation for increasing the spontaneous respiration rate. If an insufficient tidal volume or minute volume is supplied during the controlled and spontaneous part of the inspiration phase, the inspiration phase will commence immediately after the spontaneous exhalation for supplying a remaining part of the set tidal volume.

15 Claims, 1 Drawing Sheet

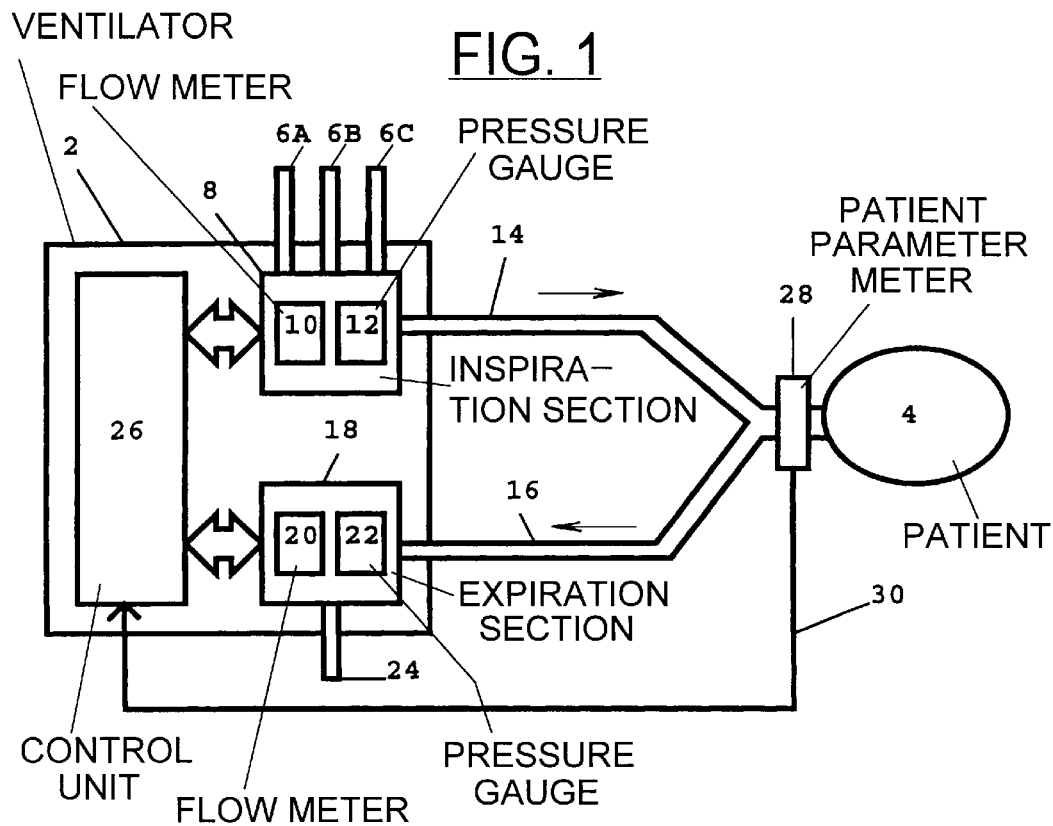
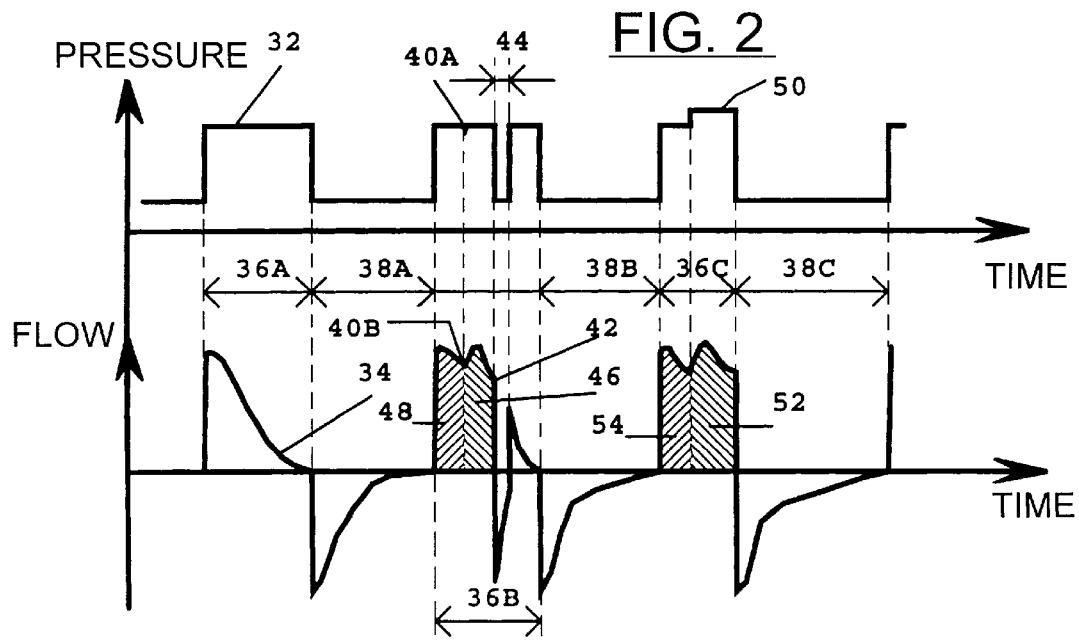

VENTILATOR WHICH ALLOWS SPONTANEOUS INHALATION AND EXPIRATION WITHIN A CONTROLLED BREATHING MODE

BACKGROUND OF THE INVENTION

1. Field of the Invention

The present invention is directed to a ventilator of the type having an inspiration section for supplying a respiratory gas to a patient's respiratory system during an inspiration phase, an expiration section for conveying respiratory gas from the respiratory system during an expiration phase, a control unit for controlling the inspiration section and the expiration section and a detector means for detecting spontaneous inhalation by the patient, connected to the control unit.

2. Description of the Prior Art

A ventilator of the above type is commercially available, known as the Servo Ventilator 300, described in an Operating Manual, Siemens-Elema AB, AG 0593 3.5, May 1993. The Servo Ventilator 300 can be set to operate in a number of different ventilation modes, such as pressure control, volume control, volume support, pressure regulated volume control, etc. One feature, selectable in all ventilation modes, is the trigger function, i.e., automatically triggering an inspiration phase dependent on the patient's breathing efforts. The ventilator detects attempts of the patient to breathe spontaneously and delivers, upon such detection, a controlled or supported inspiration (depending on the set ventilation mode). When the patient triggers in a controlled ventilation mode, the patient will be provided with a controlled breath according to the set parameters for the control mode. If such triggering occurs in a support ventilation mode, the patient may exercise some control of the respiration cycle. Some control and support modes also include a control feature for insuring that the patient receives a sufficient tidal volume or minute volume of respiratory gas.

It is also possible that the patient may try to inhale spontaneously during a controlled inspiration phase. If the pressure level is regulated in the control mode, the pressure level will be maintained by the ventilator and the inspiration phase will be completed at the same pressure level. If the tidal volume supplied to the patient is controlled, the ventilator will determine whether the patient can complete the breath, i.e., whether the patient by means of the spontaneous inhalation can reach (inhale) the set tidal volume. If the patient is incapable of completing the breath, the volume control will extend throughout the entire inspiration phase. If the patient is capable of completing the breath, the inspiration phase will be terminated and a normal exhalation phase commences.

In order to increase comfort for the patient and to accelerate any weaning of the patient from the ventilator, the supply of respiratory gas must be made in a way which guarantees a sufficient supply of respiratory gas to the patient but at the same time allows a respiration pattern which is as normal as possible for the patient. The patient will thereby be stimulated to increase spontaneous respiration and reduce dependency of the ventilator for maintaining a sufficient respiration.

SUMMARY OF THE INVENTION

An object of the present invention is to provide a ventilator of the type initially described which can provide a more natural environment for the patient's spontaneous respiration and in particular can contribute to enhance spontaneous attempts of the patient to breathe naturally, while at the same time reducing any discomfort to the patient.

This object is achieved in accordance with the invention in a ventilator of the type initially described wherein, if the detector for detecting spontaneous inhalation by the patient detects a spontaneous inhalation during a controlled inspiration phase, the control unit will, immediately after the spontaneous inhalation, control the inspiration section to interrupt the supply of respiratory gas for a specific period of time during the inspiration phase, and will control the expiration section to convey respiratory gas from the respiratory system for the specific period of time, thereby allowing the patient to spontaneously exhale for the specific period of time during the inspiration phase.

In the inventive ventilator, instead of continuing the controlled inspiration phase until it ends according to the programming, or interrupting the inspiration phase completely, the patient will, within the inspiration phase, be allowed to spontaneously exhale after the spontaneous inhalation. This will stimulate and enhance the patient's attempts at spontaneous respiration and will also increase the comfort for the patient.

The detector for detecting spontaneous inhalations may include one or more flow meters and/or one or more pressure gauges for detecting flow and/or pressure variation typical for inspiration attempts in a known manner.

In an embodiment of the ventilator in accordance with the invention, means for measuring the flow of respiratory gas are provided for measuring both the flow supplied to and the flow conveyed from the patient, and the control unit includes means for calculating a spontaneously inhaled tidal volume, and an exhaled tidal volume and controls the duration of the specific period of time such that the exhaled tidal volume is substantially equal to the spontaneous tidal volume.

In other words, the patient is allowed to exhale a volume of gas that is basically equal to the volume of gas which the patient inhaled spontaneously. The remainder of the supplied respiratory gas (supplied during the controlled part of the inspiration phase) will be conveyed from the respiratory system during the normal expiration phase.

It is preferable to limit the aforementioned specific period of time to a maximum duration, e.g. a maximum duration of 100 ms.

DESCRIPTION OF THE DRAWINGS

FIG. 1 is a schematic block diagram of a ventilator according to the invention.

FIG. 2 shows a respiratory diagram for explaining operation of the inventive ventilator, wherein a pressure curve is shown in the upper part and a flow curve is shown in the lower part.

DESCRIPTION OF THE PREFERRED EMBODIMENTS

FIG. 1 shows a ventilator 2 connected to a patient 4 for supplying respiratory gas to and conveying respiratory gas from the patient 4. The ventilator 2 can be connected to external gas sources via a first gas connection 6A, a second gas connection 6B and a third gas connection 6C. Via the gas connections 6A–6C, different gases can be supplied to the ventilator 2. Air, oxygen, nitrous oxide and other gases can be supplied. The gases supplied to the ventilator are led to an inspiration section 8 which includes control elements such as valves and mixing chambers for controlling flow pressure and mixture of respiratory gas. The components, and their operation, are well known. For instance the Servo Ventilator 300 described above includes such components. The inspiration section 8 further comprises a flow meter 10 for measuring the flow generated by the inspiration section 8 and a pressure gauge 12 for measuring the pressure generated by the inspiration section 8. During inspiration, controlled or supported, respiratory gas is conducted via an inspiration line 14 to the patient 4. The flow meter 10 can contain one flow sensor for the total flow or several flow sensors, one for each gas supplied. In the latter case the sum of the flow sensors represent the total flow measured by the flow meter 10.

During expiration, respiration gas is conveyed from the patient 4 via an expiration line 16 to an expiration section in the ventilator 2. The expiration section 18 has a valve for controlling the expiration flow and also for controlling the pressure in the expiration line 16. The expiration section 18 also has a flow meter 20 and an expiration pressure gauge 22 for measuring the flow and pressure in the expiration line 16. Expired gas is then conducted via an expiration outlet 24 either to ambient atmosphere or to an evacuation system of known kind (not shown). The function of the ventilator 2 is supervised by a control unit 26 which can include one or several microprocessors for controlling the inspiration section 8 and the expiration section 18. Pressure and/or flow can also be measured in a patient parameter meter 28 connected near the patient 4. Measurement signals of flow and/or pressure can be transferred to the control unit 26 via a signal line 30. The ventilator 2 can be a modified Servo Ventilator 300, Siemens-Elema AB, Solna, Sweden.

The diagram in FIG. 2 shows in the upper part, a pressure curve 32, and in the lower part, a flow curve 34. The diagram shows three respiratory cycles 36A–36C, 38A–38C starting with a first pressure controlled inspiration phase 36A. During this first inspiration phase 36A there is no attempt of spontaneous respiration from the patient and the expiration phase 38A follows during which the controlled inspiration pressure level is reduced to a PEEP level (similar to known pressure control modes).

A second inspiration phase 36B is then commenced and pressure is again supplied in a controlled manner. During this second inspiration phase 36B, however, the patient has suddenly inhaled spontaneously at the point indicated by the designations 40A in the pressure curve and 40B in the flow curve. The pressure is controlled so as to be maintained at the intended pressure level. As the patient reaches the end of the spontaneous inhalation, as indicated at 42 in the flow curve, the ventilator controls the inspiration section 8 and the expiration section 18 to allow a spontaneous exhalation during a specific period of time 44. During the specific period of time 44 the pressure is reduced (preferably to PEEP level) and the flow of respiratory gas is conveyed from the patient 4 through the expiration line 16 of the ventilator.

The completion of the spontaneous inhalation can be determined in a number of ways. It may be determined as a specific percentage of the peak flow value during the spontaneous inhalation. It may also be determined as a pressure increase in the pressure curve 32 (providing the pressure is allowed to vary within certain limits without immediately controlling the inspiration section to control the pressure back to the controlled level).

The duration of the specific period of time 44 can also be determined in a number of ways. It may be determined by first calculating the tidal volume 46 supplied to the patient 4 during the spontaneous inhalation and then calculating the expired volume and allow an equal volume of gas to be exhaled during the period of time 44. The specific period of time 44 may also be a specific preselected period of time, e.g. between 32 and 100 ms. Thirdly it may be determined in relation to a maximum duration of 100 ms minus the relation between inspiration and expiration times.

In this case the total supplied tidal volume (area 46+area 48) during the inspiration phase is also measured and compared with a set tidal volume. Because the supplied tidal volume in this case is less than the set tidal volume, the inspiration phase 36B will commence after the specific period of time 44 and the inspiration phase 36B is continued with the preselected pressure level. Thereafter the expiration phase 38B time is commenced as usual.

A third inspiration phase is then commenced, during which the patient 4 again inhales spontaneously. In this case a support pressure level 50 is added to the controlled pressure level for further enhancing the patient's respiration. The support level can be a specifically programmed support level for such events. It can also be equal to the PEEP level. Both this additional pressure support 50 and the maintenance of the control level as in the inspiration phase 36B can be features of the same ventilation mode. The decision as to which pressure to be applied will then be determined based on the ventilation history of the patient 4 (earlier attempts to breathe spontaneously), or on the selected pressure level or on some other combination of prerequisites.

This time the patient 4 spontaneously inhales a tidal volume 52 which is sufficient to exceed the set tidal volume minus the tidal volume 54 supplied during the controlled part of the inspiration phase 36C. The control unit 26 in the ventilator in this case the resets inspiration phase 36C and prolongs the following expiration phase 38C by the same amount of time (i.e. the time remaining of the reset inspiration phase 36C). The required level for resetting the inspiration phase 36C in this way, can be set at tidal volumes of 1.5 to 2 times the set tidal volume. If this limit is reached, it may also be preferable to reduce the controlled pressure level in the following respiration cycles in order to reduce the tidal volume which is actually supplied to the patient 4.

This specific feature of allowing the patient 4 to exhale during an inspiration phase can be used in any ventilation mode, where controlled respirations are provided to the patient 4.

Instead of tidal volume, minute volume can be utilized as a control parameter for the operation of the specific feature. Other limits, within which the minute volume over a specific number of respiration cycles or a prescribed time may vary, can be used. The basic principles are, however, the same.

Although modifications and changes may be suggested by those skilled in the art, it is the intention of the inventor to embody within the patent warranted hereon all changes and modifications as reasonably and properly come within the scope of his contribution to the art.

I claim as my invention:

1. A ventilator comprising:

a breathing tube connectable to a patient;

an inspiration section for supplying a respiratory gas at an inhalation pressure to said breathing tube during an inspiration phase;

an expiration section for conveying a respiratory gas from said breathing tube during an expiration phase;

detector means for detecting spontaneous inhalation by a patient; and control means for controlling said inspiration section and said expiration section and connected to said detector means for, if said detector means detects spontaneous inhalation during an inspiration phase controlled by said inspiration section, controlling said inspiration section immediately after said spontaneous inhalation to interrupt supply of respiratory gas to said breathing tube for a period of time during said inspiration phase to produce a pressure in said breathing tube which is less than said inhalation pressure and for controlling said expiration section to convey respiratory gas from said breathing tube for said period of time, for allowing a patient connected to said breathing tube to spontaneously exhale against said pressure which is less than said inhalation pressure for said period of time during said inspiration phase.

2. A ventilator as claimed in claim 1 wherein said detector means comprises at least one flow meter, said flow meter measuring a peak flow resulting from said spontaneous inhalation and continuing to measure flow resulting from said spontaneous inhalation after said peak flow, and wherein said control means comprises means for initiating said period of time when supply of said respiratory gas from said inspiration section is interrupted at a time when the flow measured by said at least one flow meter reaches a predetermined percentage of said peak flow.

3. A ventilator as claimed in claim 2 wherein said control means comprises means for initiating said period of time when said flow measured by said at least one flow meter is within a range of 5 through 25 percent of said peak flow.

4. A ventilator as claimed in claim 1 wherein said detector means comprises at least one pressure gauge which measures a baseline pressure of said respiratory gas in an absence of spontaneous inhalation and which measures a pressure increase caused by said spontaneous inhalation, and wherein said control means comprises means for initiating said period of time for interrupting supply of respiratory gas at a time when said pressure increase exceeds a predetermined level above said baseline pressure.

5. A ventilator as claimed in claim 4 wherein said control means comprises means for initiating said period of time when said pressure increase reaches a level of 5 cm $H_2O$ above said baseline pressure.

6. A ventilator as claimed in claim 1 further comprising flow measurement means for measuring flow of respiratory gas supplied to and conveyed from said breathing tube, and wherein said control means comprises means for calculating an inhaled tidal volume and an exhaled tidal volume arising from said spontaneous inhalation, and for controlling a duration of said period of time for causing said exhaled tidal volume to be substantially equal to said inhaled tidal volume.

7. A ventilator as claimed in claim 6 wherein said means for calculating comprises means for calculating said inhaled tidal volume arising due to said spontaneous inhalation by adding a first partial tidal volume inhaled during said inspiration phase preceding detection of said spontaneous inhalation and a second partial tidal volume inhaled after detection of said spontaneous inhalation, and wherein said control unit comprises means for resuming controlled inhalation by said inspiration section if said sum is below a predetermined tidal volume.

8. A ventilator as claimed in claim 6 wherein said control means comprises means, if said tidal volume exceeds said predetermined tidal volume by a predetermnined factor during a respiration cycle, for resetting a controlled inspiration phase by said inspiration section and for prolonging an expiration time in a first respiration cycle following resetting of said inspiration phase.

9. A ventilator as claimed in claim 8 wherein said control means comprises means for resetting said inspiration phase if said tidal volume exceeds said predetermined tidal volume by a predetermined factor in a range between 1.5 and 2.

10. A ventilator as claimed in claim 6 wherein said calculating means comprises means for calculating said inhaled tidal volume arising due to said spontaneous inhalation as an average sum of first and second partial minute volumes over a predetermined number of consecutive respiration cycles, said first partial minute volume comprising a minute volume of said respiratory gas supplied by said inspiration section preceding detection of said spontaneous inhalation and said second partial minute volume comprising a minute volume inhaled after detection of said spontaneous inhalation, and wherein said control means comprises means for resuming controlled inspiration by said inspiration section if said average sum falls below a predetermined minute volume.

11. A ventilator as claimed in claim 1 wherein said control means comprises means for limiting said period of time to a maximum duration.

12. A ventilator as claimed in claim 11 wherein said control means comprises means for limiting said period of time to a maximum duration of 100 ms.

13. A ventilator as claimed in claim 1 wherein said inspiration section comprises means for delivering a set tidal volume at a controlled pressure, and wherein said control means comprises means for automatically adjusting said controlled pressure.

14. A ventilator as claimed in claim 13 wherein said control means comprises means for determining whether a tidal volume supplied to said breathing tube exceeds an upper tidal volume limit and for, if said tidal volume exceeds said tidal volume upper limit, controlling said inspiration section for preventing any pressure increase of the respiratory gas supplied to said breathing tube.

15. A ventilator as claimed in claim 1 wherein said inspiration section comprises means for delivering a set minute volume at a controlled pressure, and wherein said control means comprises means for automatically adjusting said controlled pressure.

* * * * *